(12) United States Patent
Leadbeater et al.

(10) Patent No.: US 9,159,929 B2
(45) Date of Patent: Oct. 13, 2015

(54) RIGID AMINES

(71) Applicants: CAMBRIDGE DISPLAY TECHNOLOGY LIMITED, Cambridgeshire (GB); CDT OXFORD LIMITED, Cambridgeshire (GB)

(72) Inventors: Mark Levence Leadbeater, Depden (GB); Sophie Heidenhain, Lower Cambourne (GB); Annette Steudel, Cambridge (GB); Daniel Hicks, Cambridge (GB)

(73) Assignees: CAMBRIDGE DISPLAY TECHNOLOGY LIMITED, Cambridgeshire (GB); CDT OXFORD LIMITED, Cambridgeshire (GB)

(*) Notice: Subject to any disclaimer, the term of this patent is extended or adjusted under 35 U.S.C. 154(b) by 256 days.

(21) Appl. No.: 13/846,824

(22) Filed: Mar. 18, 2013

(65) Prior Publication Data

US 2013/0220422 A1    Aug. 29, 2013

Related U.S. Application Data

(63) Continuation of application No. 11/813,095, filed as application No. PCT/GB2005/005058 on Dec. 23, 2005, now Pat. No. 8,415,029.

(30) Foreign Application Priority Data

Dec. 29, 2004 (GB) .................................. 0428443.6
Feb. 3, 2005 (GB) .................................. 0502254.6

(51) Int. Cl.
| | |
|---|---|
| *H01L 51/54* | (2006.01) |
| *C09K 11/06* | (2006.01) |
| *C08G 73/02* | (2006.01) |
| *H01L 51/00* | (2006.01) |
| *C07D 209/88* | (2006.01) |
| *C08G 61/12* | (2006.01) |
| *C08L 65/00* | (2006.01) |
| *H05B 33/14* | (2006.01) |
| *H01L 31/0256* | (2006.01) |

(52) U.S. Cl.
CPC .......... *H01L 51/0043* (2013.01); *C07D 209/88* (2013.01); *C08G 61/121* (2013.01); *C08G 61/122* (2013.01); *C08G 61/124* (2013.01); *C08G 73/026* (2013.01); *C08L 65/00* (2013.01); *C09K 11/06* (2013.01); *H01L 31/0256* (2013.01); *H01L 51/0035* (2013.01); *H01L 51/0059* (2013.01); *H01L 51/0072* (2013.01); *H05B 33/14* (2013.01); *C08G 2261/3162* (2013.01); *C08G 2261/3241* (2013.01); *C09K 2211/1466* (2013.01); *H01L 51/0036* (2013.01); *H01L 51/0039* (2013.01); *H01L 51/0085* (2013.01); *Y02E 10/549* (2013.01)

(58) Field of Classification Search
None
See application file for complete search history.

(56) References Cited

U.S. PATENT DOCUMENTS

| | | |
|---|---|---|
| 4,539,507 A | 9/1985 | VanSlyke et al. |
| 5,150,006 A | 9/1992 | Van Slyke et al. |
| 5,432,014 A | 7/1995 | Sano et al. |
| 5,621,131 A | 4/1997 | Kreuder et al. |
| 5,723,873 A | 3/1998 | Yang |
| 5,798,170 A | 8/1998 | Zhang et al. |
| 6,083,634 A | 7/2000 | Shi |
| 6,268,695 B1 | 7/2001 | Affinito |
| 6,353,083 B1 | 3/2002 | Inbasekaran et al. |
| 6,953,628 B2 | 10/2005 | Kamatani et al. |
| 7,030,138 B2 | 4/2006 | Fujimoto et al. |
| 7,094,477 B2 | 8/2006 | Kamatani et al. |
| 7,125,998 B2 | 10/2006 | Stossel et al. |
| 7,147,935 B2 | 12/2006 | Kamatani et al. |
| 7,238,435 B2 | 7/2007 | Kamatani et al. |
| 7,250,226 B2 | 7/2007 | Tokito et al. |
| 7,329,722 B2 | 2/2008 | Vaitkeviciene et al. |
| 2002/0117662 A1 | 8/2002 | Nii |
| 2002/0182441 A1 | 12/2002 | Lamansky et al. |

(Continued)

FOREIGN PATENT DOCUMENTS

| | | |
|---|---|---|
| EP | 0 707 020 A2 | 4/1996 |
| EP | 0 842 208 | 5/1998 |
| EP | 0 901 176 A2 | 3/1999 |

(Continued)

OTHER PUBLICATIONS

Chen et al., "Recent Developments in Molecular Organic Electroluminescent Materials," *Macromol. Symp.*, 125:1-48 (1997).
Chen et al., "Triplet Exciton Confinement in Phosphorescent Polymer Light-Emitting Diodes," *Appl. Phys. Lett.*, 82(7):1006-1008 (2003).
Cleave et al., "Harvesting Singlet and Triplet Energy in Polymer LEDs," *Adv. Mat.*, 11(4):285288 (1999).
Field et al., "Bridged Triarylamines: A New Class of Heterohelicenes," *J. Org. Chem.*, 68(16):6071-6078 (2003).
Hameurlaine et al., "Synthesis of Soluble Oligocarbazole Derivatives," *Tetrahedron Letters*, 44(5):957-959 (2003).
Hellwinkel et al., "Zweifach Ortho-Verbruckte Triphenylamin-Derivate," *Chemische Berichte*, 113:358-384 (1980).

(Continued)

*Primary Examiner* — Andrew K Bohaty
(74) *Attorney, Agent, or Firm* — Marshall, Gerstein & Borun LLP

(57) ABSTRACT

A monomer for use in manufacturing a conjugated polymer, the monomer having a structure as shown formula (2):

$$X_1-(Ar_1-N-Ar_3)-X_3 \quad (2)$$
$$\phantom{X_1-(Ar_1-N}Z\phantom{)}|$$
$$\phantom{X_1-(Ar_1-NZ)}Ar_2$$

$Ar_1$, $Ar_2$ and $Ar_3$ are independently selected from optionally substituted aryl or heteroaryl, $X_1$ and $X_3$ both independently comprise a leaving group capable of participating in polymerization and Z represents a direct bond or an optionally substituted bridging atom.

37 Claims, 1 Drawing Sheet

(56) References Cited

U.S. PATENT DOCUMENTS

| | | |
|---|---|---|
| 2006/0149022 A1 | 7/2006 | Parham et al. |
| 2006/0284140 A1 | 12/2006 | Breuning et al. |

FOREIGN PATENT DOCUMENTS

| | | |
|---|---|---|
| EP | 0 947 123 | 10/1999 |
| EP | 0 949 850 | 10/1999 |
| EP | 1 229 063 A2 | 8/2002 |
| EP | 1 245 659 A1 | 10/2002 |
| EP | 1 394 188 A1 | 3/2004 |
| GB | 2 348 316 | 9/2000 |
| JP | 61-141725 | 6/1986 |
| JP | 2002-324679 A | 11/2002 |
| JP | 2003-212850 | 7/2003 |
| JP | 2005-071909 | 3/2005 |
| WO | WO-90/13148 A1 | 11/1990 |
| WO | WO-98/10621 | 3/1998 |
| WO | WO-98/57381 | 12/1998 |
| WO | WO-99/48160 | 9/1999 |
| WO | WO-99/54385 | 10/1999 |
| WO | WO-00/48258 | 8/2000 |
| WO | WO-00/53656 A1 | 9/2000 |
| WO | WO-00/55927 A1 | 9/2000 |
| WO | WO-01/19142 | 3/2001 |
| WO | WO-01/62869 | 8/2001 |
| WO | WO-01/81649 | 11/2001 |
| WO | WO-02/31896 | 4/2002 |
| WO | WO-02/44189 | 6/2002 |
| WO | WO-02/45466 | 6/2002 |
| WO | WO-02/066552 A1 | 8/2002 |
| WO | WO-02/068435 | 9/2002 |
| WO | WO-02/081448 | 10/2002 |
| WO | WO-02/084759 | 10/2002 |
| WO | WO-02/092723 | 11/2002 |
| WO | WO-02/92724 A1 | 11/2002 |
| WO | WO-03/018653 | 3/2003 |
| WO | WO-03/22908 A1 | 3/2003 |
| WO | WO-03/074628 | 9/2003 |
| WO | WO-2004/070772 A2 | 8/2004 |
| WO | WO-2004/113468 A1 | 12/2004 |

OTHER PUBLICATIONS

Ikai et al., "Highly Efficient Phosphorescence from Organic Light-Emitting Devices with an Exciton-Block Layer," *Appl. Phys. Lett.*, 79(2):156-158 (2001).

International Preliminary Report on Patentability for International Application No. PCT/GB2005/005058, dated Jul. 3, 2007.

International Search Report for International Application No. PCT/GB2005/005058, dated Apr. 3, 2006.

Jovanovic et al., "Bromination of 10-Phenylphenothiazine and 10-Phenylphenoxazine," *J. Org. Chem.*, 49:1905-1908 (1984).

Kobayashi et al., "A Novel RGB Mulitcolor Light-Emitting Polymer Display," *Snyth. Metals*, 111-112:125-128 (2000).

Lane et al., "Origin of Electrophosphorescence from a Doped Polymer Light Emitting Diode," *Phys. Rev. B.*, 63:235206-1-235206-8 (2001).

Lee et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Niu et al., "Thermal Annealing Below the Glass Transition Temperature: A General Way to Increase Performance of Light-Emitting Diodes Based on Copolyfluorenes," *Appl. Phys. Lett.*, 81(4):634-636 (2002).

O'Brien et al., "Electrophosphoresence from a Doped Polymer Light Emitting Diode," Synth. Metals, 116:379-383 (2001).

Setayesh et al., Bridgin the Gap Between Polyfluorene and Ladder-Poly-p-phenylene: Synthesis and Characterization of Poly-2,8-indenofluorene, *Macromolecules*, 33:2016-2020 (2000).

Written Opinion for International Application No. PCT/GB2005/005058, dated Apr. 3, 2006.

Yamaguchi et al., "Effects of B and C on the Ordering of $L1_0$-CoPt Thin Films," *Appl. Phys. Lett.*, 79(13):2001-2003 (2001).

Yamamoto et al., "Electrically Conducting and Thermally Stable π-Conjugated Poly(arylene)s Prepared by Organometallic Processes," *Progress in Polymer Science*, 17:1153-1205 (1993).

Yang et al., "Efficient Blue Polymer Light-Emitting Diodes from a Series of Soluble Poly(paraphenylene)s," *J. Appl. Phys.*, 79(2):934-939 (1996).

Zhang et al., "Novel Hole-Transporting Materials Based on 1,4-Bis(carbazolyl)benzene for Organic Light-Emitting Devices," *J. Mat. Chem.*, 14(5):895-900 (2004).

Zhu et al., "Synthesis of New Iridium Complexes and Their Electrophosphorescent Properties in Polymer Light-Emitting Diodes," *J. Mater. Chem.*, 13:50-55 (2003).

Combined Search and Examination Report for GB0428443.6, dated May 23, 2005.

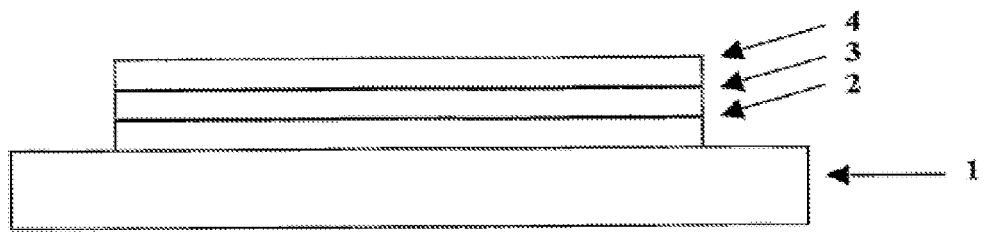

RIGID AMINES

FIELD OF INVENTION

This invention relates to amines. More particularly, this invention relates to amine monomers and polymers formed from amine monomers for use as emitters and/or charge transporters and/or host materials in opto-electrical devices.

BACKGROUND OF INVENTION

The use of triarylamine units as emitters, hole transporters and host materials in opto-electrical devices is known as will be evident from the following description of the background to the invention which outlines a basic device structure and some known materials for use in such a structure.

One class of opto-electrical devices is that using an organic material for light emission or detection. The basic structure of these devices is a light emissive organic layer, for instance a film of a poly (p-phenylenevinylene) ("PPV") or polyfluorene, sandwiched between a cathode for injecting negative charge carriers (electrons) and an anode for injecting positive charge carriers (holes) into the organic layer. The electrons and holes combine in the organic layer generating photons. In WO90/13148 the organic light-emissive material is a polymer. In U.S. Pat. No. 4,539,507 the organic light-emissive material is of the class known as small molecule materials, such as (8-hydroxyquinoline) aluminium ("Alq3"). In a practical device one of the electrodes is transparent, to allow the photons to escape the device.

A typical organic light-emissive device ("OLED") is fabricated on a glass or plastic substrate coated with a transparent first electrode such as indium-tin-oxide ("ITO"). A layer of a thin film of at least one electroluminescent organic material covers the first electrode. Finally, a cathode covers the layer of electroluminescent organic material. The cathode is typically a metal or alloy and may comprise a single layer, such as aluminium, or a plurality of layers such as calcium and aluminium. Other layers can be added to the device, for example to improve charge injection from the electrodes to the electroluminescent material. For example, a hole injection layer such as poly (ethylene dioxythiophene)/polystyrene sulfonate (PEDOT-PSS) or polyaniline may be provided between the anode and the electroluminescent material. When a voltage is applied between the electrodes from a power supply one of the electrodes acts as a cathode and the other as an anode.

In operation, holes are injected into the device through the anode and electrons are injected into the device through the cathode. The holes and electrons combine in the organic electroluminescent layer to form an exciton which then undergoes radiative decay to give light.

For organic semiconductors, important characteristics are the binding energies, measured with respect to the vacuum level of the electronic energy levels, particularly the "highest occupied molecular orbital" (HOMO) and the "lowest unoccupied molecular orbital" (LUMO) level. These can be estimated from measurements of photoemission and particularly measurements of the electrochemical potentials for oxidation and reduction. It is well understood in this field that such energies are affected by a number of factors, such as the local environment near an interface, and the point on the curve (peak) from which the value is determined. Accordingly, the use of such values is indicative rather than quantitative.

The optical and electronic properties of an organic semiconductor are highly dependent on the energy of the aforementioned HOMO and LUMO levels. Furthermore, these energy levels are highly dependent on the chemical structure of the organic semiconductor. By selecting suitable materials, or combinations of materials, device performance can be improved.

For example, one way of improving efficiency of devices is to provide hole and electron transporting materials. WO 99/48610 discloses blending of hole transporting polymers, electron transporting polymers and electroluminescent polymers. A 1:1 copolymer of dioctylfluorene and triphenylamine is disclosed as a hole transporting polymer in this document. The type of charge transporting material which is most effective will be dependent on the HOMO and LUMO of the other components in the device.

Although there has been much improvement in the efficiency of devices using charge transporting materials, there is always a desire to develop new charge transporting materials to further improving efficiency when compared with existing devices.

Another focus in the field of polymer OLEDs is the development of full colour displays for which red, green and blue emissive materials are required. By "red electroluminescent material" is meant an organic material that by electroluminescence emits radiation having a wavelength in the range of 600-750 nm, preferably 600-700 nm, more preferably 610-650 nm and most preferably having an emission peak around 650-660 nm. By "green electroluminescent material" is meant an organic material that by electroluminescence emits radiation having a wavelength in the range of 510-580 nm, preferably 510-570 nm. By "blue electroluminescent material" is meant an organic material that by electroluminescence emits radiation having a wavelength in the range of 400-500 nm, more preferably 430-500 nm.

One drawback with existing polymer OLED displays relevant to this development is the relatively short lifetime of blue emissive materials known to date (by "lifetime" is meant the time for the brightness of the OLED to halve at constant current when operated under DC drive).

In one approach, the lifetime of the emissive material may be extended by optimisation of the OLED architecture; for example lifetime of the blue material may in part be dependant on the cathode being used. However, the advantage of selecting a cathode that improves blue lifetime may be offset by disadvantageous effects of the cathode on performance of red and green materials. For example, Synthetic Metals 111-112 (2000), 125-128 discloses a full colour display wherein the cathode is LiF/Ca/Al. The present inventors have found that this cathode is particularly efficacious with respect to the blue emissive material but which shows poor performance with respect to green and, especially, red emitters.

Another approach is development of novel blue electroluminescent materials. For example, WO 00/55927, which is a development of WO 99/48160, discloses a blue electroluminescent polymer of formula (a):

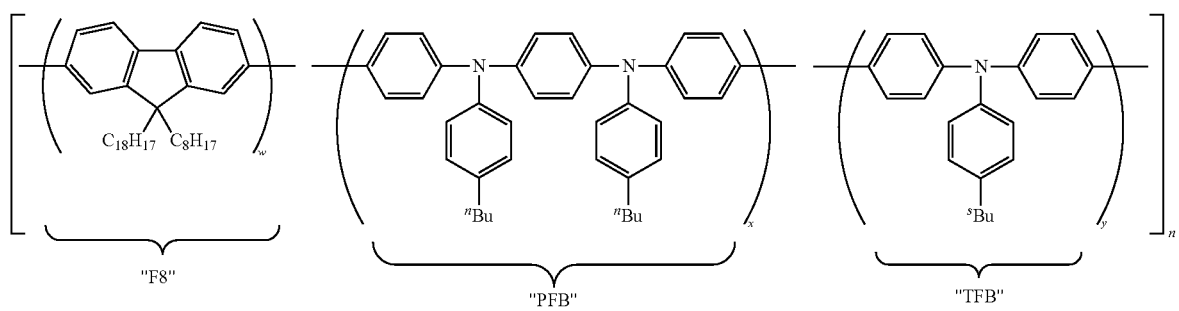

(a)

wherein w+x+y=1, w≥0.5, 0≤x+y≤0.5 and n≥2.

In essence, the separate polymers disclosed in WO 99/48160 are combined into a single molecule. The F8 repeat unit is provided for the purpose of electron injection; the TFB unit is provided for the purpose of hole transport; and the PFB repeat unit is provided as the emissive unit. The combination of units into a single polymer may be preferable to a blend. For example, intramolecular charge transport may be preferable to intermolecular charge transport. Potential difficulties of phase separation in blends is also avoided.

WO 02/92723 and WO02/92724 disclose replacement of some of the F8 repeat units in the polymer illustrated above with 9,9-diarylfluorene repeat units, in particular diphenylfluorene (DPF) repeat units which has surprisingly been found to improve lifetime of the polymer.

WO 99/54385 and EP 1229063 disclose copolymers of fluorenes and PFB-type triarylamine repeat units. EP 1229063 discloses a copolymer of F8:TFB in a 70:30 ratio.

Although there has been much improvement in the lifetime of blue emissive materials there is always a desire to develop new blue emissive materials to further improve lifetime of the polymer.

Phosphorescent materials are also useful and in some applications may be preferable to fluorescent materials. One type of phosphorescent material comprises a host and a phosphorescent emitter in the host. The emitter may be bonded to the host or provided as a separate component in a blend.

Numerous hosts for phosphorescent emitters are described in the prior art including "small molecule" hosts such as 4,4'-bis(carbazol-9-yl)biphenyl), known as CBP, and (4,4',4''-tris(carbazol-9-yl)triphenylamine), known as TCTA, disclosed in Ikai et al. (*Appl. Phys. Lett.*, 79 no. 2, 2001, 156); and triarylamines such as tris-4-(N-3-methylphenyl-N-phenyl)phenylamine, known as MTDATA. Homopolymers are also known as hosts, in particular poly(vinyl carbazole) disclosed in, for example, Appl. Phys. Lett. 2000, 77(15), 2280; polyfluorenes in Synth. Met. 2001, 116, 379, Phys. Rev. B 2001, 63, 235206 and Appl. Phys. Lett. 2003, 82(7), 1006; poly[4-(N-4-vinylbenzyloxyethyl, N-methylamino)-N-(2,5-di-tert-butylphenylnapthalimide] in Adv. Mater. 1999, 11(4), 285; and poly(para-phenylenes) in J. Mater. Chem. 2003, 13, 50-55.

A problem with known host-phosphor systems is that the host may quench emission from the phosphor. In general, the lower the triplet energy level of the host (relative to the phosphor) then the more likely quenching will occur. Polymerisation can exacerbate this problem by reducing the triplet energy level of a monomer when forming a host polymer. Accordingly, there is a need to produce materials with a high triplet energy level for use as hosts in phosphorescent systems.

Such host-emitter systems are not limited to phosphorescent devices. A wide range of fluorescent low molecular weight metal complexes are known and have been demonstrated in organic light emitting devices [see, e.g., Macromol. Sym. 125 (1997) 1-48, U.S. Pat. No. 5,150,006, U.S. Pat. No. 6,083,634 and U.S. Pat. No. 5,432,014].

As with phosphorescent systems, a problem with known host-fluorescent emitter systems is that the host may quench emission from the fluorescent emitter. It is advantageous to provide a host having a higher LUMO than that of the emitter to inject electrons into the emitter. It is advantageous to provide a host having a lower HOMO than that of the emitter to inject holes into the emitter. Accordingly, there is a need to produce materials with a large band gap between the HOMO and LUMO for use as hosts in fluorescent systems.

Another factor affecting the performance of opto-electonic devices is morphology of the films which make up the device. For semiconductive organic materials it is advantageous to have an amorphous rather than a crystalline film. However, it is desirable not to have too much disorder in the film in order to achieve a device with better performance. Accordingly, there is a desire to produce materials with better film forming characteristics.

Another problem with known devices results from charge migration past the emitting regions. Accordingly, it is sometimes useful to provide charge-blocking materials. There is a desire to produce materials with better charge blocking characteristics. A low HOMO may aid in blocking holes while a high LUMO may aid in blocking electrons.

It is an aim of the present invention to solve one or more of the problems outlined above.

SUMMARY OF INVENTION

According to a first aspect of the present invention there is provided a monomer for use in manufacturing a conjugated polymer, the monomer having a structure as shown formula (2):

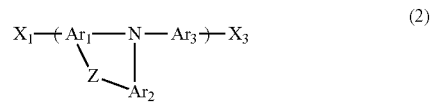

(2)

wherein $Ar_1$, $Ar_2$ and $Ar_3$ are independently selected from optionally substituted aryl or heteroaryl, $X_1$ and $X_3$ both independently comprise a leaving group capable of participating in polymerisation and Z represents a direct bond or an optionally substituted bridging atom.

One or more of $Ar_1$, $Ar_2$ and $Ar_3$ may comprise a substituent independently selected from the group consisting of optionally substituted, branched or linear alkyl, aryl, perfluoroalkyl, thioalkyl, cyano, alkoxy, heteroaryl, alkylaryl and arylalkyl groups.

One or more of $Ar_1$, $Ar_2$ and $Ar_3$ may comprise an optionally substituted phenyl group.

The monomer may have a structure as shown in formula (3):

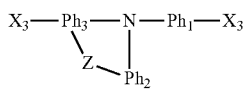

(3)

wherein $Ph_1$, $Ph_2$ and $Ph_1$ are independently optionally substituted phenyl groups, $X_3$ independently comprises a leaving group capable of participating in polymerisation and Z represents a direct bond or an optionally substituted bridging atom.

The monomer may have a structure as shown in formula (4):

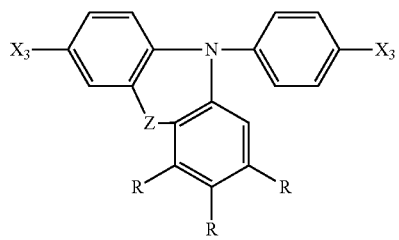

(4)

wherein $X_3$ independently comprises a leaving group capable of participating in polymerisation, R is independently selected from H or a substituent group and Z represents a direct bond or an optionally substituted bridging atom. One or more of R may be independently selected from the group consisting of optionally substituted, branched or linear alkyl, aryl, perfluoroalkyl, thioalkyl, cyano, alkoxy, heteroaryl, alkylaryl and arylalkyl groups. Preferably R is independently selected from H or $C_{1-10}$ alkyl.

One or more of $X_1$, $X_2$ and $X_3$ may consist of a leaving group capable of participating in polymerisation.

The monomer may have a structure as shown in formula (5):

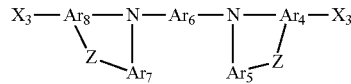

(5)

wherein $Ar_4$, $Ar_5$, $Ar_6$, $Ar_7$ and $Ar_8$ are independently optionally substituted aryl or heteroaryl groups, $X_3$ independently comprise a leaving group capable of participating in polymerisation and Z independently represents a direct bond or an optionally substituted bridging atom. $X_3$ may comprise an optionally substituted aryl or heteroaryl group.

One or more of $Ar_4$, $Ar_5$, $Ar_6$, $Ar_7$ and $Ar_8$ may comprise an optionally substituted phenyl ring.

One or more of $Ar_4$, $Ar_5$, $Ar_6$, $Ar_7$ and $Ar_8$ may consist of an optionally substituted phenyl ring. In another embodiment, only one group Z is present in the monomer of formula (5).

The monomer may have a structure as shown in formula (7):

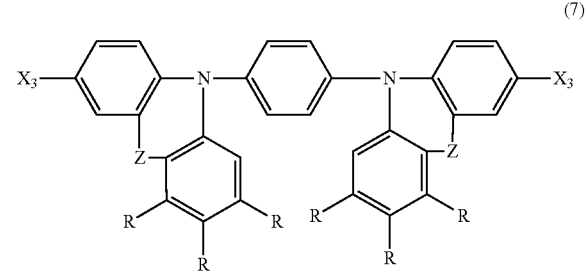

(7)

wherein $X_3$ independently comprise a leaving group capable of participating in polymerisation, R is independently selected from H or a substituent group and Z independently represents a direct bond or an optionally substituted bridging atom. One or more of R may be independently selected from the group consisting of optionally substituted, branched or linear alkyl, aryl, perfluoroalkyl, thioalkyl, cyano, alkoxy, heteroaryl, alkylaryl and arylalkyl groups. Preferably R is independently selected from H or $C_{1-10}$ alkyl.

$X_3$ may comprise an optionally substituted aryl or heteroaryl group.

Preferably the leaving groups are capable of participating in metal insertion type polymerisation. Leaving groups that are capable of participating in metal insertion type polymerisation include boron derivative groups, halogens and sulfonates. A preferred boron derivative is a boronic acid or boronic ester. A preferred halogen is bromine. A preferred sulfonate is triflate, mesylate, phenyl sulfonate or tosylate.

The monomer may have a structure as shown formula (9):

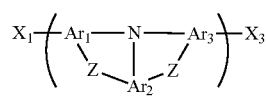

(9)

wherein $Ar_1$, $Ar_2$ and $Ar_3$ are independently selected from optionally substituted aryl or heteroaryl, $X_1$ and $X_3$ both independently comprise a leaving group capable of participating in polymerisation and Z independently represents a direct bond or an optionally substituted bridging atom. According to this structure, two links between a pendent aryl group and aryl groups in the backbone are provided.

It will be understood that two links between a pendent aryl group and aryl groups in the backbone may be provided in all of the other embodiments disclosed herein.

Preferably, both Z in formula 9 independently represent an optionally substituted bridging atom.

The monomer may have a structure as shown formula (10):

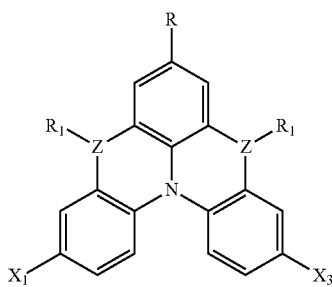

(10)

wherein $X_1$ and $X_3$ both independently comprise a leaving group capable of participating in polymerisation, R is selected from hydrogen or a substituent group and $R_1$ is independently selected from a vinyl group, an alkyl group or hydrogen and Z represents an optionally substituted bridging atom. R may be selected from the group consisting of optionally substituted, branched or linear alkyl, aryl, perfluoroalkyl, thioalkyl, cyano, alkoxy, heteroaryl, alkylaryl and arylalkyl groups. Preferably R is independently selected from hydrogen or $C_{1-10}$ alkyl.

Preferably if bridging atoms are present then one or both bridging atoms are carbon. One or both bridging atoms may be independently substituted with a vinyl group, an alkyl group or hydrogen. One or both bridging atoms may be a heteroatom. This structure is more easily oxidised. The heteroatom may be N, O or S. Preferably the bridging atom is C. The C atom may have an optionally substituted aryl or heteroaryl substituent thereon Preferably the C atom has a Ph substituent. The substituent on the C atom may have a substituent R thereon which aids solubility, for example an alkyl group.

Embodiments having bridging atoms rather than direct bonds may be better hole transporters as there is less twist in the structure resulting in a higher HOMO level.

According to a second aspect of the present invention there is provided a conjugated polymer formed from a monomer as described herein. The conjugated polymer may comprise a repeat unit having a structure according to formula (11):

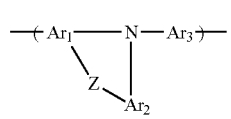

(11)

The repeat units may be linked in a conjugated polymer such that each repeat unit is directly linked to aryl groups on either side in the polymer backbone. That is, aryl groups in one repeat unit are directly linked to aryl groups in an adjacent repeat unit along the polymer backbone.

A "repeat" unit as referred to herein may be the residue of a monomer which was incorporated into the polymer upon polymerisation. However, the present invention is not so limited. A "repeat unit" as referred to herein may be a part of the residue of a monomer which was incorporated into the polymer upon polymerisation.

Preferably, the conjugated polymer comprises one or more repeat units shown in formulae 12-17:

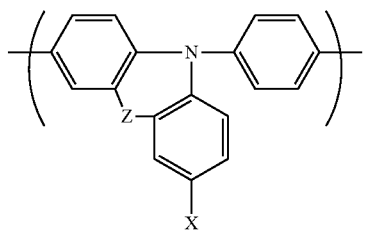

(12)

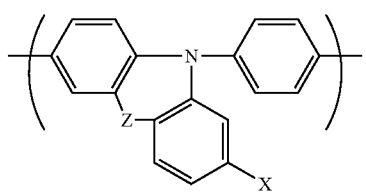

(13)

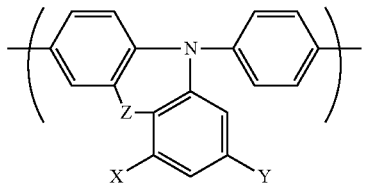

(14)

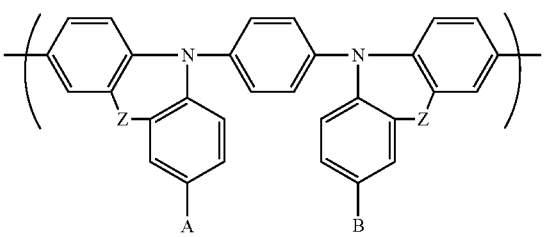

(15)

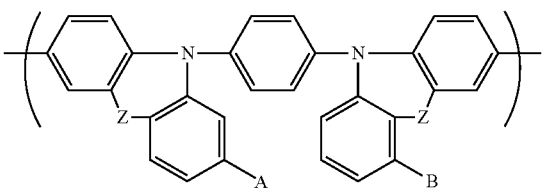

(16)

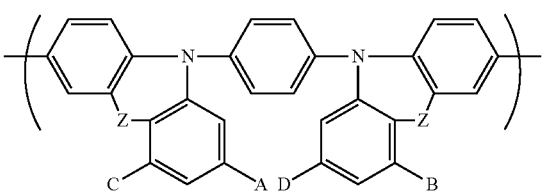

(17)

wherein X, Y, A, B, C and D are independently selected from H or a substituent group and Z independently represents a direct bond or an optionally substituted bridging atom. Preferably, Z represents a direct bond. One or more of X, Y, A, B, C and D may be independently selected from the group consisting of optionally substituted, branched or linear alkyl, aryl, perfluoroalkyl, thioalkyl, cyano, alkoxy, heteroaryl, alkylaryl and arylalkyl groups. Preferably, X, Y, A, B, C and D are $C_{1-10}$ alkyl.

The conjugated polymer may be at least one of an emissive polymer, a hole transporting polymer and an electron transporting polymer. Optionally, the conjugated polymer is a copolymer comprising two or more different repeat units. The conjugated polymer may comprise at least two of a hole transporting repeat unit, an electron transporting repeat unit and an emissive repeat unit.

According to a third aspect of the present invention there is provided a blend comprising at least one conjugated polymer as described herein and at least one other conjugated polymer. Preferably the blend comprises at least two of a hole transporting polymer, an electron transporting polymer and an emissive polymer.

According to a fourth embodiment of the present invention there is provided an emissive material comprising a host matrix and an emissive dopant, the host matrix comprising a conjugated polymer as described herein. The emissive dopant may be chemically bound to the host. Alternatively, the emissive dopant may be provided as a separate component in a blend. The emissive dopant may be phosphorescent. Alternatively, the emissive dopant may be fluorescent. The emissive dopant may be a small molecule. In particular, the emissive dopant may be a metal complex.

According to a fifth aspect of the present invention there is provided an opto-electrical device comprising one or more of: a conjugated polymer as described herein; a blend as described herein; and an emissive material as described herein. The opto-electrical device may be an organic light emissive diode with the conjugated polymer, blend or emissive material being provided in a layer between two electrodes. The layer may be an emissive layer of the device or the layer may be a separate layer from an emissive layer of the device.

Alternatively, the opto-electrical device may be a photovoltaic device.

According to a sixth aspect of the present invention there is provided a monomer, a conjugated polymer, a blend, an emissive material, or an opto-electrical device as described herein, wherein Z represents an optionally substituted bridging atom.

According to a seventh aspect of the present invention there is provided a composition comprising a conjugated polymer, a blend, or an emissive material as described herein, wherein said composition does not contain a metal complex.

According to an eighth aspect of the present invention there is provided an opto-electrical device comprising the aforementioned composition.

According to a ninth aspect of the present invention there is provided a composition comprising a conjugated polymer including a repeat unit having a structure according to formula (11):

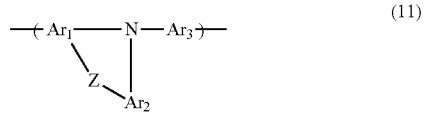

(11)

wherein $Ar_1$ and $Ar_2$ are independently selected from optionally substituted aryl or heteroaryl and Z represents a direct bond or an optionally substituted bridging atom, wherein said composition does not contain a metal complex.

According to a tenth aspect of the present invention there is provided an opto-electrical device comprising a composition comprising a conjugated polymer including a repeat unit having a structure according to formula (11):

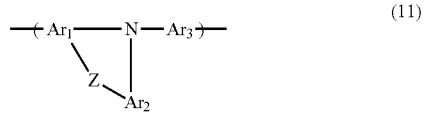

(11)

wherein $Ar_1$ and $Ar_2$ are independently selected from optionally substituted aryl or heteroaryl and Z represents a direct bond or an optionally substituted bridging atom, wherein said composition does not contain a metal complex.

The important feature of arylamine containing polymers according to the present invention is that at least two bonds are provided between a pendent group and the polymer backbone. Embodiments of the invention relate to units comprising triarylamines such as "TFB" and "PFB" but with a pendent aryl group being bound to an aryl group in the polymer backbone. The provision of an additional bond compared with prior art arylamine units causes the resultant unit to be more rigid and more planar with less twisting. In particular, an additional bond is introduced between a pendent aryl group and a backbone aryl group in the arylamine unit. Accordingly, the pendent aryl group is conjugated to the backbone through the additional bond. This structural change increases conjugation and shifts the LUMO and HOMO levels so as to increase the optical and electronic band gap.

The particular use of a polymer comprising a repeat unit according to the present invention will depend on what other repeat units are provided in the polymer chain or what other polymers or small molecules are present in a blend. For example, by co-polymerising units according to the present invention the Tg and other properties can be controlled.

Furthermore, the type of substituents on the repeat units according to the present invention will affect the functionality of the repeat units. For example, electron withdrawing or electron donating groups may be selectively substituted into the structure to fine tune functional effects according to a required use.

Embodiments of the present invention may have none, one, two or three bridging carbons. Vinyl substituents on the bridging carbon(s) give the possibility of thermal crosslinking. The bridging carbon(s) restrict phenyl ring rotation and increase the rigidity of the molecule. In a polymer this results in a higher glass transition temperature.

An alternative configuration not according to the present invention comprises a repeat unit of the following formula:

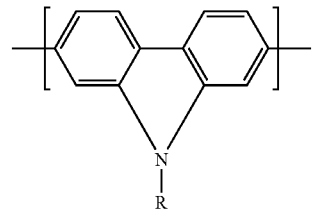

However, this unit has different properties to that of embodiments of the present invention because the pendent aryl group R is not conjugated to the aromatic rings in the backbone through an additional bond as in embodiments of the present invention. Embodiments of the present invention have an N atom in the backbone with an additional bond between the aryl group pendent from the N atom and an aryl group in the backbone. This different structure can lead to significant differences in optical and electronic behaviour. The conjugation of the lone pair on the N atom in the backbone and the use of this lone pair is important to the functional properties of polymers of the present invention. In embodiments of the present invention conjugation with the pendent group may be via alternating double and single bonds through the additional bond or via a lone pair of electrons on the N atom.

BRIEF DESCRIPTION OF THE DRAWINGS

Embodiments of the present invention will now be described by way of example only with reference to the accompanying drawing in which:

FIG. 1 shows an organic light emitting device according to an embodiment of the present invention.

DETAILED DESCRIPTION OF EMBODIMENTS OF THE INVENTION

The device shown in FIG. 1 comprises a transparent glass or plastic substrate 1, an anode 2 of indium tin oxide and a cathode 4. An electroluminescent layer 3 is provided between anode 2 and cathode 4.

Further layers may be located between anode 2 and cathode 3, such as charge transporting, charge injecting or charge blocking layers.

In particular, it is desirable to provide a conductive hole injection layer formed of a doped organic material located between the anode 2 and the electroluminescent layer 3 to assist hole injection from the anode into the layer or layers of semiconducting polymer. Examples of doped organic hole injection materials include poly(ethylene dioxythiophene) (PEDT), in particular PEDT doped with polystyrene sulfonate (PSS) as disclosed in EP 0901176 and EP 0947123, or polyaniline as disclosed in U.S. Pat. No. 5,723,873 and U.S. Pat. No. 5,798,170.

If present, a hole transporting layer located between anode 2 and electroluminescent layer 3 preferably has a HOMO level of less than or equal to 5.5 eV, more preferably around 4.8-5.5 eV.

If present, an electron transporting layer located between electroluminescent layer 3 and cathode 4 preferably has a LUMO level of around 3-3.5 eV.

Electroluminescent layer 3 may consist of the electroluminescent material alone or may comprise the electroluminescent material in combination with one or more further materials. In particular, the electroluminescent material may be blended with hole and/or electron transporting materials as disclosed in, for example, WO 99/48160. Alternatively, the electroluminescent material may be covalently bound to a charge transporting material.

Cathode 4 is selected from materials that have a workfunction allowing injection of electrons into the electroluminescent layer. Other factors influence the selection of the cathode such as the possibility of adverse interactions between the cathode and the electroluminescent material. The cathode may consist of a single material such as a layer of aluminium. Alternatively, it may comprise a plurality of metals, for example a bilayer of calcium and aluminium as disclosed in WO 98/10621, elemental barium disclosed in WO 98/57381, Appl. Phys. Lett. 2002, 81(4), 634 and WO 02/84759 or a thin layer of dielectric material to assist electron injection, for example lithium fluoride disclosed in WO 00/48258 or barium fluoride, disclosed in Appl. Phys. Lett. 2001, 79(5), 2001. In order to provide efficient injection of electrons into the device, the cathode preferably has a workfunction of less than 3.5 eV, more preferably less than 3.2 eV, most preferably less than 3 eV.

Optical devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device is preferably encapsulated with an encapsulant (not shown) to prevent ingress of moisture and oxygen. Suitable encapsulants include a sheet of glass, films having suitable barrier properties such as alternating stacks of polymer and dielectric as disclosed in, for example, WO 01/81649 or an airtight container as disclosed in, for example, WO 01/19142. A getter material for absorption of any atmospheric moisture and/or oxygen that may permeate through the substrate or encapsulant may be disposed between the substrate and the encapsulant.

In a practical device, at least one of the electrodes is semi-transparent in order that light may be absorbed (in the case of a photoresponsive device) or emitted (in the case of an OLED). Where the anode is transparent, it typically comprises indium tin oxide. Examples of transparent cathodes are disclosed in, for example, GB 2348316.

The embodiment of FIG. 1 illustrates a device wherein the device is formed by firstly forming an anode on a substrate followed by deposition of an electroluminescent layer and a cathode. However it will be appreciated that the device of the invention could also be formed by firstly forming a cathode on a substrate followed by deposition of an electroluminescent layer and an anode.

The polymers of the present invention may be provided in the emissive layer and/or may be provided in a separate layer (such as electron or hole transporting layers). Furthermore, the arylamine repeat units of the present invention may be provided in a homopolymer or a copolymer and/or in a blend of different polymers. In this regard, various possible repeat units and/or different polymers may be used in conjunction with the arylamine units of the present invention. Some of these are discussed below and it is envisaged that any combination (blend, copolymer or separate layer) of one or more of the repeat units/polymers discussed below may be used with repeat units/polymers according to the present invention depending on the desired function and the type of device desired.

Polymers may comprise a first repeat unit selected from arylene repeat units, in particular: 1,4-phenylene repeat units as disclosed in J. Appl. Phys. 1996, 79, 934; fluorene repeat units as disclosed in EP 0842208; indenofluorene repeat units as disclosed in, for example, Macromolecules 2000, 33(6), 2016-2020; and spirofluorene repeat units as disclosed in, for example EP 0707020. Each of these repeat units is optionally substituted. Examples of substituents include solubilising groups such as $C_{1-20}$ alkyl or alkoxy; electron withdrawing groups such as fluorine, nitro or cyano; and substituents for increasing glass transition temperature (Tg) of the polymer.

Particularly preferred polymers comprise optionally substituted, 2,7-linked fluorenes, most preferably repeat units of formula (18):

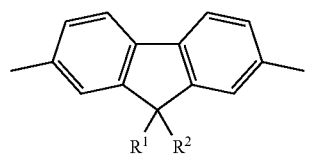

(18)

wherein $R^1$ and $R^2$ are independently selected from hydrogen or optionally substituted alkyl, alkoxy, aryl, arylalkyl, heteroaryl and heteroarylalkyl. More preferably, at least one of $R^1$ and $R^2$ comprises an optionally substituted $C_4$-$C_{20}$ alkyl or aryl group.

A polymer comprising the first repeat unit may provide one or more of the functions of hole transport, electron transport and emission depending on which layer of the device it is used in and the nature of co-repeat units.

A homopolymer of the first repeat unit, such as a homopolymer of 9,9-dialkylfluoren-2,7-diyl, may be utilised to provide electron transport. Alternatively, a homopolymer comprising a repeat unit according to an embodiment of the present invention may be utilised to provide electron transport.

A copolymer comprising a first repeat unit and a triarylamine repeat unit according to an embodiment of the present invention may be utilised to provide hole transport and/or emission.

Particularly preferred hole transporting polymers of this type are AB copolymers of the first repeat unit and a triarylamine repeat unit.

A copolymer comprising a first repeat unit and heteroarylene repeat unit may be utilised for charge transport or emission. Preferred heteroarylene repeat units are selected from formulae 19-33:

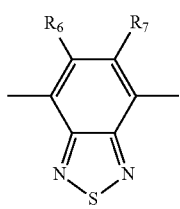

19 wherein $R_6$ and $R_7$ are the same or different and are each independently hydrogen or a substituent group, preferably alkyl, aryl, perfluoroalkyl, thioalkyl, cyano, alkoxy, heteroaryl, alkylaryl or arylalkyl. For ease of manufacture, $R_6$ and $R_7$ are preferably the same. More preferably, they are the same and are each a phenyl group.

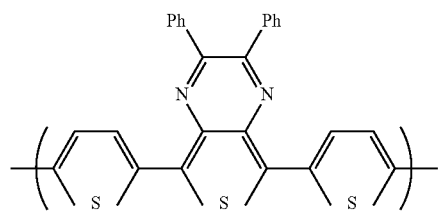

20

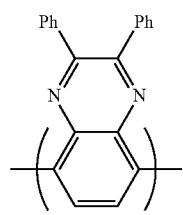

21

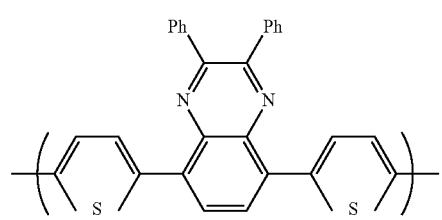

22

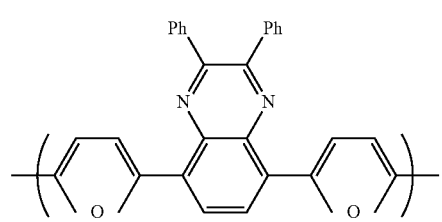

23

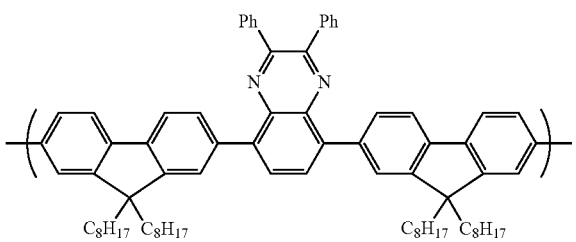

24

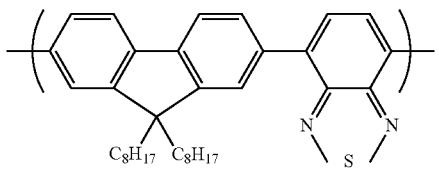

25

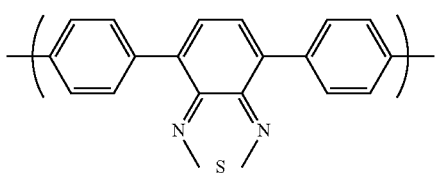

26

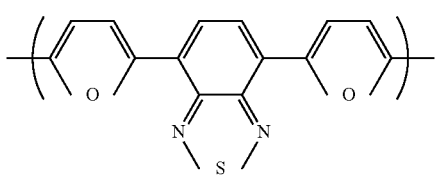

27

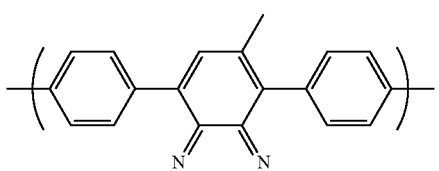

28

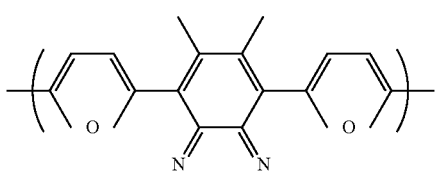

29

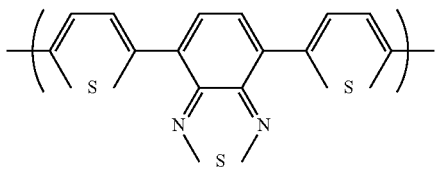

30

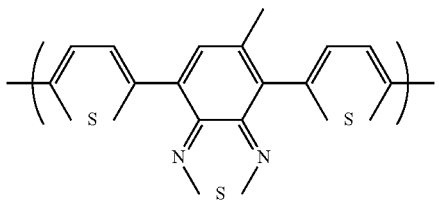

31

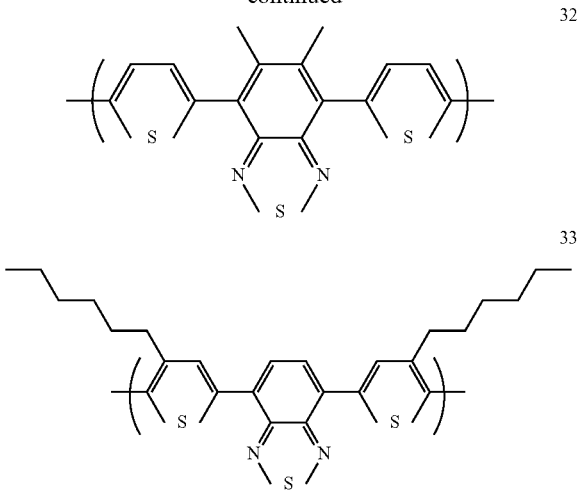

Electroluminescent copolymers may comprise an electroluminescent region and at least one of a hole transporting region and an electron transporting region as disclosed in, for example, WO 00/55927 and U.S. Pat. No. 6,353,083. If only one of a hole transporting region and electron transporting region is provided then the electroluminescent region may also provide the other of hole transport and electron transport functionality.

The different regions within such a polymer may be provided along the polymer backbone, as per U.S. Pat. No. 6,353,083, or as groups pendent from the polymer backbone as per WO 01/62869.

Preferred methods for preparation of these polymers are Suzuki polymerisation as described in, for example, WO 00/53656 and Yamamoto polymerisation as described in, for example, T. Yamamoto, "Electrically Conducting And Thermally Stable π-Conjugated Poly(arylene)s Prepared by Organometallic Processes", Progress in Polymer Science 1993, 17, 1153-1205. These polymerisation techniques both operate via a "metal insertion" wherein the metal atom of a metal complex catalyst is inserted between an aryl group and a leaving group of a monomer. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine It will therefore be appreciated that repeat units and end groups comprising aryl groups as illustrated throughout this application may be derived from a monomer carrying a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halides, other leaving groups capable of participating in metal insertion include tosylate, mesylate, phenyl sulfonate and triflate.

A single polymer or a plurality of polymers may be deposited from solution to form layer 5. Suitable solvents for polyarylenes, in particular polyfluorenes, include mono- or poly-alkylbenzenes such as toluene and xylene. Particularly preferred solution deposition techniques are spin-coating and inkjet printing.

Spin-coating is particularly suitable for devices wherein patterning of the electroluminescent material is unnecessary—for example for lighting applications or simple monochrome segmented displays.

Inkjet printing is particularly suitable for high information content displays, in particular full colour displays Inkjet printing of OLEDs is described in, for example, EP 0880303.

If multiple layers of the device are formed by solution processing then the skilled person will be aware of techniques to prevent intermixing of adjacent layers, for example by crosslinking of one layer before deposition of a subsequent layer or selection of materials for adjacent layers such that the material from which the first of these layers is formed is not soluble in the solvent used to deposit the second layer.

Preferred phosphorescent metal complexes comprise optionally substituted complexes of formula (34):

wherein M is a metal; each of $L^1$, $L^2$ and $L^3$ is a coordinating group; q is an integer; r and s are each independently 0 or an integer; and the sum of $(a \cdot q)+(b \cdot r)+(c \cdot s)$ is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet states (phosphorescence). Suitable heavy metals M include:

lanthanide metals such as cerium, samarium, europium, terbium, dysprosium, thulium, erbium and neodymium; and d-block metals, in particular those in rows 2 and 3 i.e. elements 39 to 48 and 72 to 80, in particular ruthenium, rhodium, palladium, rhenium, osmium, iridium, platinum and gold.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission colour is determined by the choice of the metal. The sharp emission is generally narrow, resulting in a pure colour emission useful for display applications.

The d-block metals form organometallic complexes with carbon or nitrogen donors such as porphyrin or bidentate ligands of formula (35):

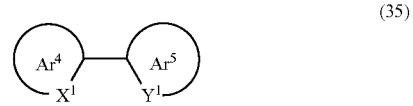

wherein $Ar^4$ and $Ar^5$ may be the same or different and are independently selected from optionally substituted aryl or heteroaryl; $X^1$ and $Y^1$ may be the same or different and are independently selected from carbon or nitrogen; and $Ar^4$ and $Ar^5$ may be fused together. Ligands wherein $X^1$ is carbon and $Y^1$ is nitrogen are particularly preferred.

Examples of Bidentate Ligands are Illustrated Below:

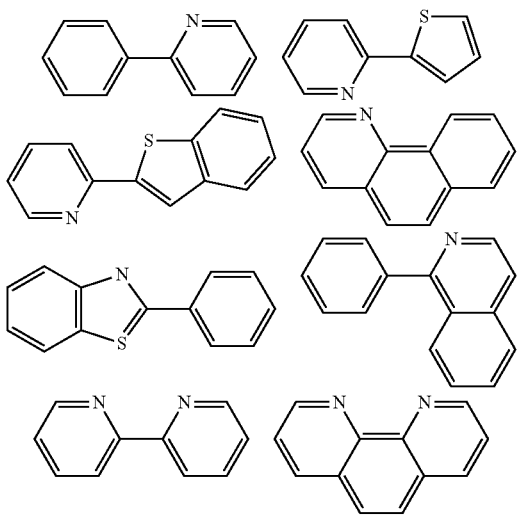

Each of $Ar^4$ and $Ar^5$ may carry one or more substituents. Particularly preferred substituents include fluorine or trifluoromethyl which may be used to blue-shift the emission of the complex as disclosed in WO 02/45466, WO 02/44189, US 2002-117662 and US 2002-182441; alkyl or alkoxy groups as disclosed in JP 2002-324679; carbazole which may be used to assist hole transport to the complex when used as an emissive material as disclosed in WO 02/81448; bromine, chlorine or iodine which can serve to functionalise the ligand for attachment of further groups as disclosed in WO 02/68435 and EP 1245659; and dendrons which may be used to obtain or enhance solution processability of the metal complex as disclosed in WO 02/66552. The presence of substituents to improve solubility of the metal complex is particularly desirable in order to facilitate solution processing of a composition of the metal complex and a soluble host polymer according to the invention. This composition may be a mixture of the host and dopant, or alternatively the substituted metal complex may be chemically bound to the host material as set out below.

Other ligands suitable for use with d-block elements include diketonates, in particular acetylacetonate (acac); triarylphosphines and pyridine, each of which may be substituted.

Main group metal complexes show ligand based, or charge transfer emission. For these complexes, the emission colour is determined by the choice of ligand as well as the metal.

The host material and metal complex may be combined in the form of a physical blend. Alternatively, the metal complex may be chemically bound to the host material. In the case of a polymeric host, the metal complex may be chemically bound as a substituent attached to the polymer backbone, incorporated as a repeat unit in the polymer backbone or provided as an end-group of the polymer as disclosed in, for example, EP 1245659, WO 02/31896, WO 03/18653 and WO 03/22908.

Embodiments of the present invention can also be used as hosts for fluorescent emitters. A wide range of fluorescent low molecular weight metal complexes may be used with the present invention. A preferred example is tris-(8-hydroxyquinoline)aluminium. Suitable ligands for di or trivalent metals include: oxinoids, e.g. with oxygen-nitrogen or oxygen-oxygen donating atoms, generally a ring nitrogen atom with a substituent oxygen atom, or a substituent nitrogen atom or oxygen atom with a substituent oxygen atom such as 8-hydroxyquinolate and hydroxyquinoxalinol-10-hydroxybenzo (h) quinolinato (II), benzazoles (III), schiff bases, azoindoles, chromone derivatives, 3-hydroxyflavone, and carboxylic acids such as salicylato amino carboxylates and ester carboxylates. Optional substituents include halogen, alkyl, alkoxy, haloalkyl, cyano, amino, amido, sulfonyl, carbonyl, aryl or heteroaryl on the (hetero) aromatic rings which may modify the emission colour.

According to embodiments of the present invention an additional bond is incorporated between a pendent aryl group and a backbone aryl group as compared with known arylamines. The resultant structure has wide ranging advantages over the prior art arylamines. Without wishing to be bound by theory it is thought that the additional linkage (Z) increases the rigidity and planarity of the structure, which increases conjugation in a conjugated polymer leading to better charge transporting properties and better film forming capacity. The band gap between HOMO and LUMO levels is increased when compared with known arylamines producing a bluer emitter. Furthermore, an increase in LUMO energy level may be advantageous for electron transport/injection while a decrease in HOMO energy level may be advantageous for hole transport/injection. Also, quenching in host-emitter systems may be reduced due to an increase in triplet energy level and increase in the band gap between HOMO and LUMO. The change in HOMO and LUMO levels may also improve charge-blocking characteristics. Accordingly, it is evident that the new arylamine units may be useful as emitters, hole transporters, electron transporters, charge blockers (particularly electron blockers) and host materials in phosphorescent and fluorescent systems.

While this invention has been particularly shown and described with reference to preferred embodiments thereof, it will be understood by those skilled in the art that various changes in form and details may be made therein without departing from the scope of the invention as defined by the appended claims.

Reaction Schemes

Monomers may be synthesized according to the following reaction schemes:

Scheme 1

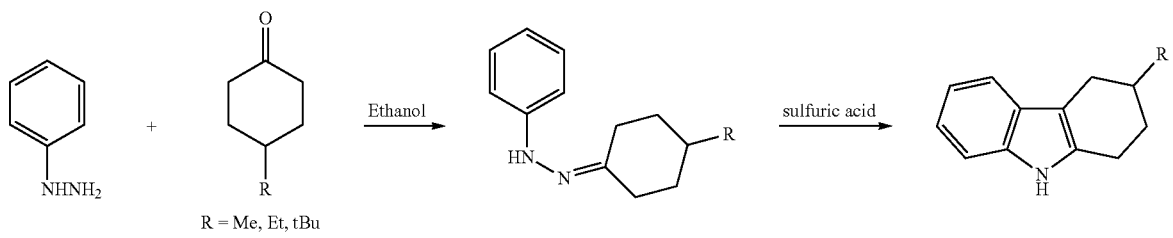

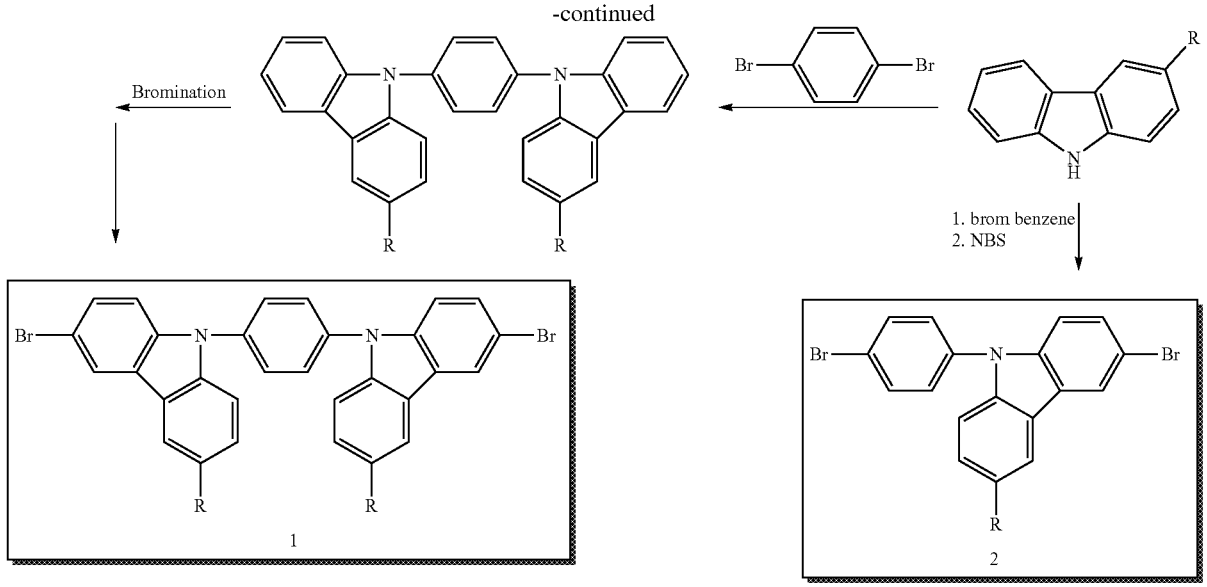
Scheme 2
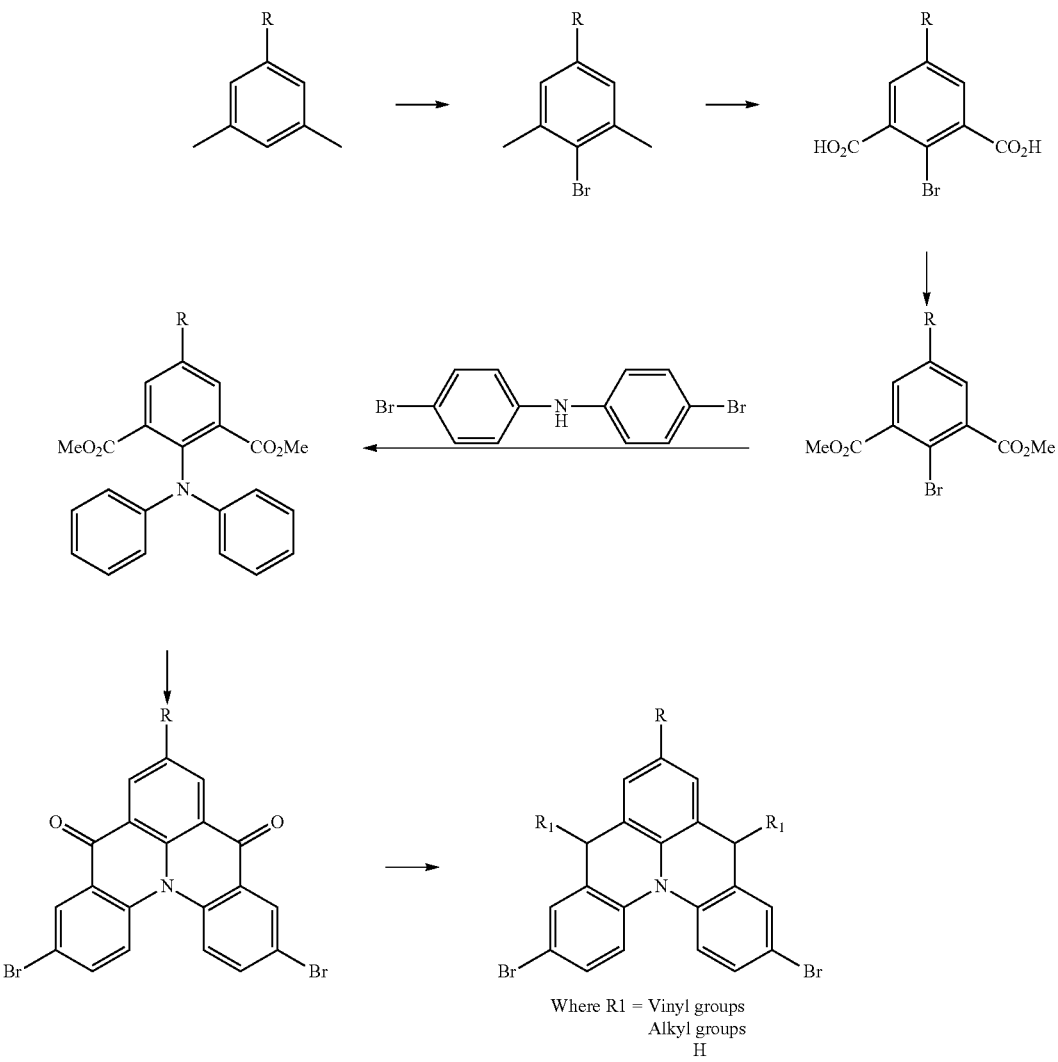
Where R1 = Vinyl groups
Alkyl groups
H

Monomers of Scheme 2 may be prepared according to the method set out in J. Org. Chem. 2003, 68, 16, 6071-6078.

The monomers may then be incorporated into polymers using Suzuki polymerisation.

EXAMPLES

Monomer Example 1

Monomer 1 according to the invention, which is shown below, was synthesised according to Scheme 1:

Monomer 1

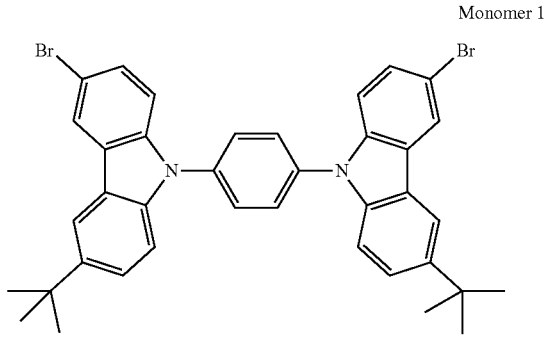 [SMILES: CC(C)(C)c1ccc2c(c1)c1cc(Br)ccc1n2-c1ccc(-n2c3ccc(Br)cc3c3cc(C(C)(C)C)ccc32)cc1]

Monomer 1 was synthesised in a four stage process as set out below.

Stage 1

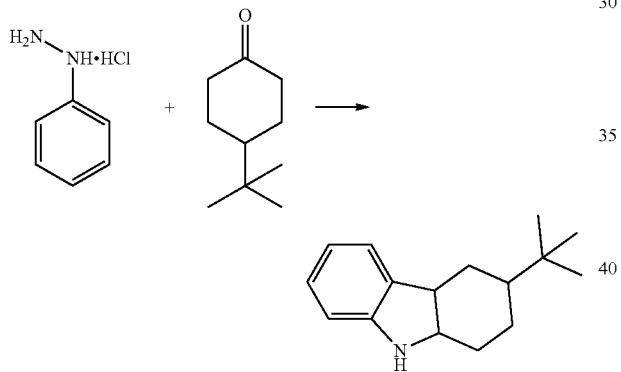

Phenyl hydrazine hydrochloride (30 g, 0.28 mol), tert-butyl cyclohexanone (42.79 g, 0.28 mol) and acetic acid (600 mL) were added to a round bottom flask, equipped with a nitrogen line and condenser. The reagents were stirred at room temperature for 30 mins and then warmed to 30° C. After 20 mins, the heating was increased to 35° C. and held at this temperature. After 30 mins, the heating was increased to 40° C. for a further 6 hours and then warmed to 70° C. overnight. The reaction mixture was allowed to cool to room temperature and then toluene was added. The organic phase was washed with water, NaHCO$_3$ and finally water. The solvent was evaporated and the product recrystallized from hexane. Yielding 24.29 g (~55% yield) of desired material.

Stage 2

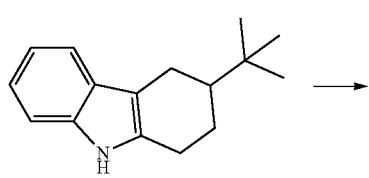

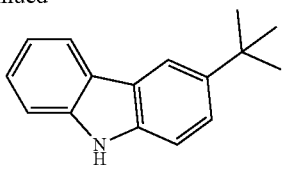

A 2 L flask equipped with an over head stirrer, nitrogen bubbler and reflux condenser was charged with tetrahydrobutylcarbonate (79 g, 0.34 mol), 10% Pd/C (11.1 g, 0.004 mol) and trimethylbenzene. The reaction mixture was heated to reflux (180-190° C.) for 30 h and then allowed to cool to room temperature. Upon cooling the reaction mixture crystallised out. The crystallised solution was diluted with toluene and filtered through a Buchner. The solution was filtered several times through filter paper and then 1 L of hexane was added. The colourless solid which formed was filtered off affording 58.98 g of product at 99.7% purity (yield 95%).

Stage 3

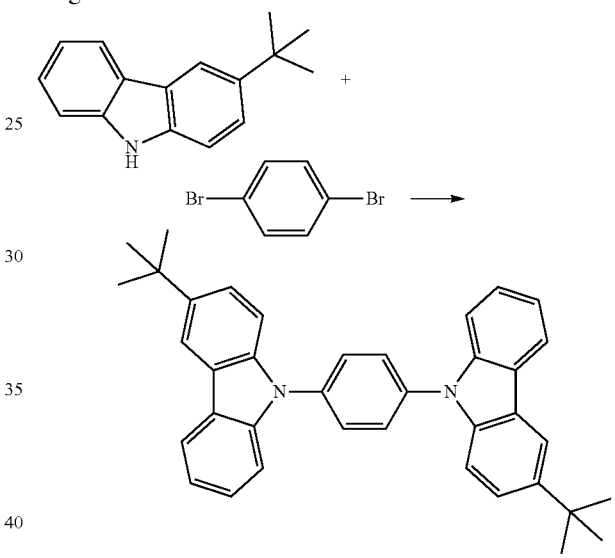

A 500 mL flask charged with tert-butylcarbazole (10 g, 0.045 mol), dibromobenzene (4.95 g, 0.021 mol); palladium acetate (101 mg, 1 mol %); and toluene (100 mL) was degassed for 0.5 h with nitrogen. Tert-butyl triphenylphosphine (4.6 mL, 5 mol %) was then added and the solution stirred. After 30 mins, potassium carbonate (19 g, 0.084 mol) was added and the reaction heated to 130° C. for 4 days. The reaction was allowed to cool to room temperature and then extracted with water. The organic phase was dried (MgSO$_4$) and evaporated under vacuum Recrystallization from toluene/acetonitrile gave 9.31 g of desired material (yield 85%).

Stage 4

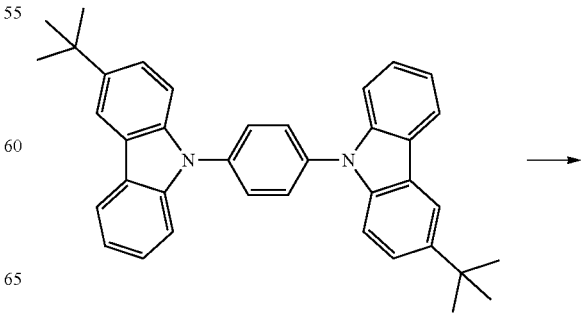

-continued

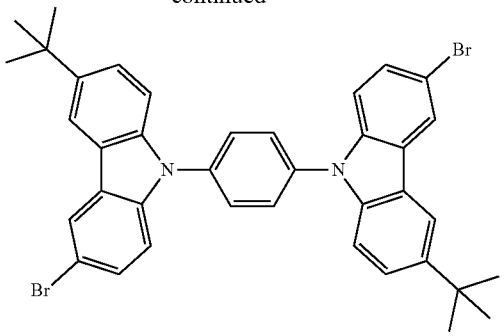

To a cooled (−5° C., internal flask temp) solution of material prepared in stage 3 (20 g, 0.48 mol) in dichloromethane (350 mL) was added iodine (catalytic quantity) and then portion wise addition of N-bromosuccinimide (13.73 g, 0.077 mol). The reaction temperature was kept below 15° C. throughout the addition of NBS. The reaction mixture was extracted with water. The organic phase was separated off, dried (MgSO$_4$) and evaporated to dryness to afford a brown solid. Recrystallization from toluene/IPA (1 L/200 mL) gave 19.6 g of Monomer 1 (yield 75% yield).

Modelling

Monomer 1 was studied using a commercially available modelling package. Calculations were performed to obtain the HOMO, LUMO and Eg of Monomer 1. Furthermore, calculations were performed for F8 and an F8-TFB co-polymer using the same modelling package so as to determine the relative values. In this regard, it is to be noted that modelling values will be inherently approximate but the relative values of the three polymers will give a good indication of the energy level structure of the new monomer/polymer compared to the known materials.

Calculations were performed for monomer to tetramer and extrapolated to infinite chain length to gain results for a long chain polymers. All calculations were performed using AM1 to calculate the conformations for an isolated molecule in a vacuum, followed by a Zindo calculation for the same system (using N/2 occupied and N/2 unoccupied states, where N=number of pi electrons) to calculate the molecular orbitals and energies.

1) AM1 in Ampac program package
Ampac 5.0 User's Manual, C 1994 Semichem, 7128 Summit, Shawnee, Kans. 66216

2) ZINDO from Gaussian software:
Gaussian 98, Revision A.9,
M. J. Frisch, G. W. Trucks, H. B. Schlegel, G. E. Scuseria, M. A. Robb, J. R. Cheeseman, V. G. Zakrezewski, J. A. Montgomery, Jr., R. E. Stratmann, J. C. Burant, S. Dapprich, J. M. Millam, A. D. Daniels, K. N. Kudin, M. C. Strain, O. Farkas, J. Tomasi, V. Barone, M. Cossi, R. Cammi, B. Mennucci, C. Pomelli, C. Adamo, S. Clifford, J. Ochterski, G. A. Petersson, P. Y. Ayala, Q. Cui, K. Morokuma, D. K. Malick, A. D. Rabuck, K. Raghavachari, J. B. Foresman, J. Cioslowski, J. V. Ortiz, A. G. Baboul, B. B. Stefanov, G. Liu, A. Liashenko, P. Piskorz, I. Komaromi, R. Gomperts, R. L. Martin, D. J. Fox, T. Keith, M. A. Al-Laham, C. Y. Peng, A. Nanayakkara, M. Challacombe, P. M. W. Gill, B. Johnson, W. Chen, M. W. Wong, J. L. Andres, C. Gonzales, M. Head-Gordon, E. S. Replogle, and J. A. Pople, Gaussian, Inc., Pittsburgh Pa., 1998.

The results for HOMO, LUMO and Eg are summarized in the table below showing the extrapolated values for the polymers:

|    | HOMO(ext) | LUMO(ext) | EG(ext) |
|----|-----------|-----------|---------|
| F8 | −6.94     | −0.61     | 3.41    |

It can be seen that the HOMO of Monomer 1 is even deeper than that of F8. Accordingly, it is expected that Monomer 1 will act as a hole blocker. The LUMO of Monomer 1 is even shallower than that of F8-TFB. Accordingly, it is expected that Monomer 1 will act as an electron blocker. The energy gap for Monomer 1 is higher than both that of F8 and F8-TFB. Accordingly, it will have a much bluer emission.

Modelling results indicated that the most stable conformation for Monomer 1 is one in which the bonds from N to the carbazole group and the bonds from N to the phenyl ring are all in the same plane—i.e. the N is sp2 bonded.

The modelling indicated that for an homopolymer derived from Monomer 1, the HOMO extends along the backbone of the polymer chain and the LUMO is confined to neighbouring carbazole units (but not on the hydrogens).

The N atoms in the backbone act as a "block" for the "LUMO". The LUMO is found where it can extend most fully—on the two linked carbazole units where the monomers are connected (this is a lower energy site than the phenyl rings between the carbazole units). To achieve a lower LUMO level—i.e. one into which electron injection will be easier—the electron wavefunction needs to be less confined or restricted, e.g. by adding F8s (or other similar groups as outlined earlier in the description) to either side of the monomer unit.

The HOMO level is strongest on the N atoms. It extends along the backbone between N atoms since the maximum separation of two neighbouring Ns is a maximum of only two benzene rings. Substituting the central phenyl of Monomer 1 with an F8 unit (or other similar groups as outlined earlier in the description) would act to reduce the ionisation potential of this material.

The results of the modelling for polymers comprising a repeat unit derived from Monomer 1 show that it is much bluer than either of F8 or F8-TFB co-polymer. This repeat unit has a very deep HOMO and a very shallow LUMO and thus it may be used as an interlayer material for blocking electrons, holes and/or excitons. That is, embodiments of the present invention may be provided in a separate layer between the anode and/or cathode and an emitting layer. Furthermore, it may be useful as a host material for triplet emitters.

Polymer Example 1

A copolymer (Polymer 1) having 65% F8, 30% DPF, and 5% Monomer 1 was formed by Suzuki polymerisation according to the method described in WO 00/53656.

The HOMO and LUMO of Polymer 1 were measured using cyclic voltametery:

HOMO level is very deep (similar to F8): 5.52 eV

LUMO level is shallow (similar to F8): 2.13 eV

The similarity to F8 suggests that both measured HOMO and LUMO levels are for F8 rather than the Monomer 1.

Polymer Example 2

An AB copolymer of 2,5-dioctylbenzene and the repeat unit derived from Monomer 1 (Polymer 2) was prepared by Suzuki polymerisation according to the method described in WO 00/53656 and the reaction scheme set out below, to give a polymer having a weight average molecular weight (Mw) of 57000 Daltons:

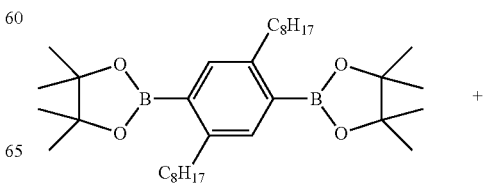

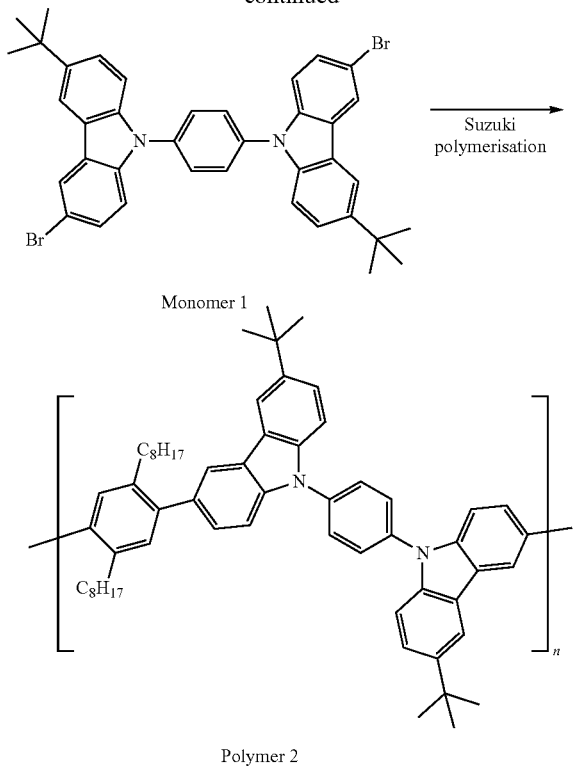

Monomer 1

Suzuki polymerisation

Polymer 2

Device Example

Fluorescent Device

A device was formed according to the process set out below.

Poly(ethylene dioxythiophene)/poly(styrene sulfonate) (PEDT/PSS), available from H C Starck of Leverkusen, Germany as Baytron P® was deposited over an indium tin oxide anode supported on a glass substrate (available from Applied Films, Colorado, USA) by spin coating. Polymer 1 according to the invention was deposited over the layer of PEDT/PSS by spin-coating from xylene solution to a thickness of around 65 nm A Ba/Al cathode was formed over polymer 1 by evaporating a first layer of barium to a thickness of up to about 10 nm and a second layer of aluminium barium to a thickness of about 100 nm over the semiconducting polymer. Finally, the device was sealed using a metal enclosure containing a getter that was placed over the device and glued onto the substrate in order to form an airtight seal.

A second device was prepared as above, except that a hole transporting layer of F8-TFB (shown below) was deposited over the PEDT/PSS layer by spin coating from xylene solution to a thickness of about 10 nm and heated at 180° C. for 1 hour prior to deposition of Polymer 1. Based on the PL emissions of F8, it is likely that emission in this device was a combination of F8 and TFB emission from the interlayer, indicating that the band gap of the repeat unit of the invention as derived from Monomer 1 is higher than F8.

Phosphorescent Host Example

A 1% solution in toluene of Polymer 2, doped with 7.5% IrD (illustrated below) as disclosed in WO 02/66552 was spun on Spectrasil glass to give a film of 60 nm. As a comparative example, a film was spun of CBP, doped with 10% IrD. As can be seen from the photoluminescent quantum yield (PLQY) measurements (see Table below), no quenching of green phosphorescence occurred. Additionally, no change in emission colour was observed based on 1931 Commision Internationale de L'Eclairage, chromaticity coordinates (CIE) coordinates, thus demonstrating the efficacy of polymers according to the invention as hosts for electrophosphorescent devices.

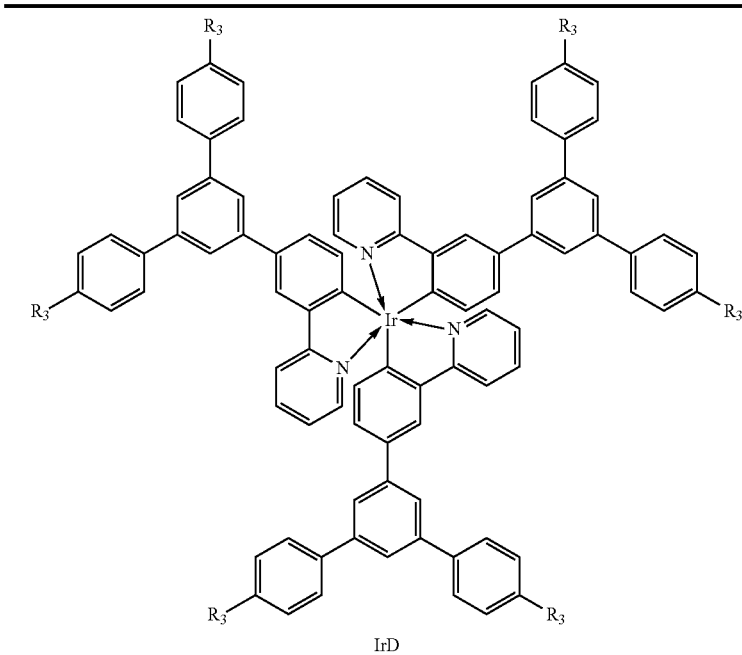

IrD

|  | Host | IrD | PLQY | CIEx | CIEy |
|---|---|---|---|---|---|
| Comparative Example | CBP | 10% | 77% | 0.33 | 0.59 |
| Example 1 | Polymer 2 | 7.5% | 72% | 0.3 | 0.59 |

The invention claimed is:

1. A conjugated polymer formed from a monomer having a structure as shown in formula (5):

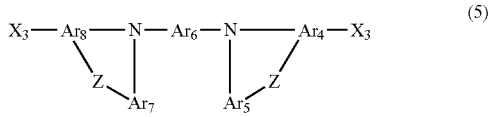

(5)

wherein $Ar_4$, $Ar_5$, $Ar_6$, $Ar_7$ and $Ar_8$ are independently optionally substituted aryl or heteroaryl groups, $X_3$ comprise a leaving group capable of participating in polymerization and Z represents an optionally substituted bridging atom, and Z is not in the polymer backbone.

2. A conjugated polymer according to claim 1, wherein one or more of $Ar_4$, $Ar_5$, $Ar_6$, $Ar_7$ and $Ar_8$ comprise an optionally substituted phenyl ring.

3. A conjugated polymer according to claim 1, wherein one or more of $Ar_4$, $Ar_5$, $Ar_6$, $Ar_7$ and $Ar_8$ consist of an optionally substituted phenyl ring.

4. A conjugated polymer according to claim 1, the monomer having a structure as shown in formula (7):

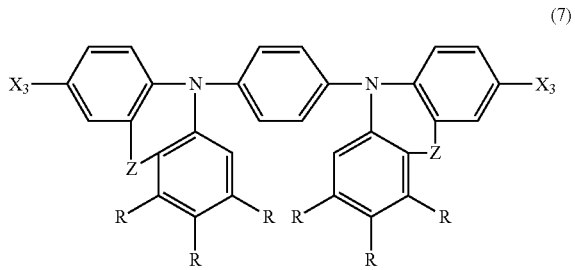

(7)

wherein each R is independently selected from H or a substituent group.

5. A conjugated polymer according to claim 4, wherein one or more of R is independently selected from the group consisting of optionally substituted, branched or linear alkyl, optionally substituted aryl, perfluoroalkyl, optionally substituted thioalkyl, cyano, optionally substituted alkoxy, optionally substituted heteroaryl, optionally substituted alkylaryl and optionally substituted arylalkyl groups.

6. A conjugated polymer according to claim 4, wherein R is independently selected from H or $C_{1-10}$ alkyl.

7. A conjugated polymer according to claim 1, wherein the leaving groups $X_3$ are capable of participating in metal insertion type polymerization.

8. A conjugated polymer according to claim 7, wherein the leaving groups capable of participating in metal insertion type polymerization are independently selected from a boron derivative, a halogen, a triflate, a mesylate, a phenyl sulphonate and a tosylate.

9. A conjugated polymer according to claim 8, wherein the boron derivative is a boronic acid or boronic ester.

10. A conjugated polymer according to claim 8, wherein the halogen is bromine.

11. A conjugated polymer according to claim 1, wherein the conjugated polymer is at least one of an emissive polymer, a hole transporting polymer and an electron transporting polymer.

12. A conjugated polymer according to claim 1, wherein the conjugated polymer is a copolymer comprising two or more different repeat units.

13. A conjugated polymer according to claim 12, comprising at least two of a hole transporting repeat unit, an electron transporting repeat unit and an emissive repeat unit.

14. A blend comprising at least one conjugated polymer according to claim 1 and at least one other conjugated polymer.

15. A blend according to claim 14, comprising at least two of a hole transporting polymer, an electron transporting polymer and an emissive polymer.

16. An emissive material comprising a host matrix and an emissive dopant, the host matrix comprising a conjugated polymer as claimed in claim 1.

17. An emissive material according to claim 16, wherein the emissive dopant is chemically bound to the host.

18. An emissive material according to claim 16, wherein the emissive dopant is provided as a separate component in a blend.

19. An emissive material according to claim 16, wherein the emissive dopant is phosphorescent.

20. An emissive material according to claim 16, wherein the emissive dopant is fluorescent.

21. An emissive material according to claim 16, wherein the emissive dopant is a small molecule.

22. An emissive material according to claim 16, wherein the emissive dopant is a metal complex.

23. An opto-electrical device including a conjugated polymer according to claim 1.

24. An opto-electrical device according to claim 23, the opto-electrical device being an organic light emissive diode comprising an anode, a cathode and wherein the conjugated polymer is provided in a layer between the anode and cathode.

25. An opto-electrical device according to claim 24, wherein the conjugated polymer is a hole transporter, an electron transporter and/or an emissive material in the opto-electrical device.

26. An opto-electrical device according to claim 24, wherein the opto-electrical device comprises an emissive layer and optionally one or more additional layers comprising organic semi-conductive material between the anode and the cathode, wherein the conjugated polymer is provided in one or more of the emissive layer and the one or more additional layers.

27. An opto-electrical device according to claim 26, wherein the conjugated polymer is provided in the emissive layer of the device.

28. An opto-electrical device according to claim 26, wherein the conjugated polymer is provided in the one or more additional layers.

29. An opto-electrical device according to claim 26, wherein the conjugated polymer or blend is provided in a layer between the anode and the emissive layer for transporting holes.

30. An opto-electrical device according to claim 26, wherein the conjugated polymer or blend is provided in a layer between the cathode and the emissive layer for transporting electrons.

31. An opto-electrical device according to claim 23, the opto-electrical device being a photovoltaic device.

32. A composition comprising a conjugated polymer according to claim 1, wherein said composition does not contain a metal complex.

33. An opto-electrical device comprising the composition of claim 32.

34. A method of forming a conjugated polymer comprising the step of polymerizing the monomer of formula (5):

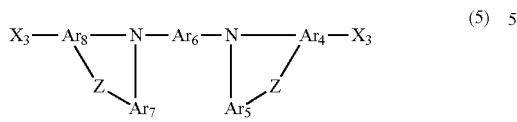

(5)

wherein $Ar_4$, $Ar_5$, $Ar_6$, $Ar_7$ and $Ar_8$ are independently optionally substituted aryl or heteroaryl groups, $X_3$ comprise a leaving group capable of participating in polymerization and Z independently represents a direct bond or an optionally substituted bridging atom, and Z is not in the polymer backbone.

35. A method according to claim 34 wherein the polymer is a copolymer and the method comprises the step of polymerizing the monomer of formula (5) with one or more comonomers for forming one or more co-repeat units of the polymer.

36. A method according to claim 34 wherein the polymerization is a metal-catalyzed polymerization.

37. A method according to claim 36 wherein the metal catalyst is a nickel or palladium catalyst.

* * * * *